United States Patent [19]
Dondlinger

[11] Patent Number: 5,836,918
[45] Date of Patent: Nov. 17, 1998

[54] SLEEVED SUCTION DEVICE

[76] Inventor: Steven C. Dondlinger, 5513 Knoll Dr., Edina, Minn. 55436

[21] Appl. No.: 456,535

[22] Filed: Jun. 1, 1995

[51] Int. Cl.⁶ .................................................. A61M 8/00
[52] U.S. Cl. ...................... 604/171; 604/43; 128/207.14; 128/207.15
[58] Field of Search ............................... 604/171, 43, 35, 604/176, 177, 53; 128/207.14, 207.15, 207.16

[56] References Cited

U.S. PATENT DOCUMENTS

| | | | |
|---|---|---|---|
| 4,062,363 | 12/1977 | Bonner, Jr. | 604/171 |
| 4,327,723 | 5/1982 | Frankhouser | 604/53 |
| 4,327,735 | 5/1982 | Hampson | 604/171 |
| 4,551,137 | 11/1985 | Osborne | 604/171 |
| 4,795,426 | 1/1989 | Jones | 604/53 |
| 4,836,199 | 6/1989 | Palmer | 604/163 |
| 4,850,350 | 7/1989 | Jackson | 604/171 |
| 5,073,164 | 12/1991 | Hollister et al. | 604/53 |
| 5,215,522 | 6/1993 | Page et al. | 604/35 |
| 5,460,613 | 10/1995 | Ulrich et al. | 604/35 |

*Primary Examiner*—Richard J. Apley
*Assistant Examiner*—Justine R. Yu
*Attorney, Agent, or Firm*—Hugh D. Jaeger

[57] ABSTRACT

A protective positionable flexible cover or sleeve for suction apparatuses where a suction catheter or other suction device is covered prior to and subsequent to suction procedures to prevent contamination of the suction catheter or other suction device for subsequent use, and for prevention of contamination transfer to medical workers and health facility environs.

3 Claims, 8 Drawing Sheets

SLEEVED SUCTION DEVICE

BACKGROUND OF THE INVENTION

1. Field of the Invention

The present invention is for a medical device, and more particularly, pertains to a suction catheter having a positionable flexible cover.

2. Description of the Prior Art

Prior art suction catheters generally have been incorporated for one time use, or more laboriously, can be reused after proper sanitation and cleaning. Often suction catheters were reused with the same patient a short time after withdrawal without resterilization or particular care of the suction catheter. Often the end of the once used suction catheter would be left in the open air where airborne viral or other bacterial contamination would come in contact with the often damp suction catheter which acted as a depository for such airborne items. Placing of a used and contaminated or unused contaminated suction catheter on a support surface, such as a table or tray, also violated anti-contaminant procedures. The contamination problem is not only involved with the problem of contamination of a suction catheter, but also includes the problem of transfer of disease bearing bacteria, viruses, and the like from a withdrawn suction catheter to medical workers and to medical facility environs, such as an operating room or hospital room.

Clearly, what is needed is a suction catheter which does not allow contamination of the environs or of the suction catheter itself. The present invention overcomes the described problems associated with suction catheter pollution by providing a sleeved suction device.

SUMMARY OF THE INVENTION

The general purpose of the present invention is a sleeved suction device.

According to one embodiment of the present invention, there is provided a sleeved suction device, including flexible cover and rigid end members aligned over and about the entire length of a flexible suction catheter. The flexible cover member, at its proximal end, connects to a suction tube member leading to a suction power source. The rigid end member and distal portion of the flexible cover member are manually drawn back along the length of the suction catheter to reveal the suction catheter or other suction device for use in a suction procedure. Subsequently, the rigid end member and distal portion of the flexible cover are repositioned distally to cover the used and/or contaminated suction catheter.

One significant aspect and feature of the present invention is a sleeved suction device having a suction catheter aligned inside of a flexible cover member. The flexible cover member slideably positions along a suction catheter to reveal a suction tube for use in a suction procedure. The flexible cover member also protects an unused or used suction catheter member from contamination by its external environs. Also, the flexible cover member which protects the external environs and personnel from a contaminated suction catheter.

Another significant aspect and feature of the present invention is a sleeved suction device having a tubular rigid end. The sleeved suction device can also have a semi-rigid end member. The bendable end member having a memory and which can function as a suction catheter guide.

Yet another significant aspect and feature of the present invention is a flexible cover member for use with a suction valve which incorporates a vent tube which passes through the flexible cover member.

Still another significant aspect and feature of the present invention is a flexible cover member incorporated for use with a tonsil type sucking device.

A further significant aspect and feature of the present invention is a sleeved suction device having a hanging loop or hook.

Having thus described embodiments of the present invention, it is the principal object of the present invention to provide a sleeved suction device with either a rigid end or a semi-rigid end.

One object of the present invention is the rigid end which prevents collapse of the sleeve while suction is on. The open area of this rigid piece does not collapse with suction and allows air to be drawn from the outside instead of pulling air out of the sleeve.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
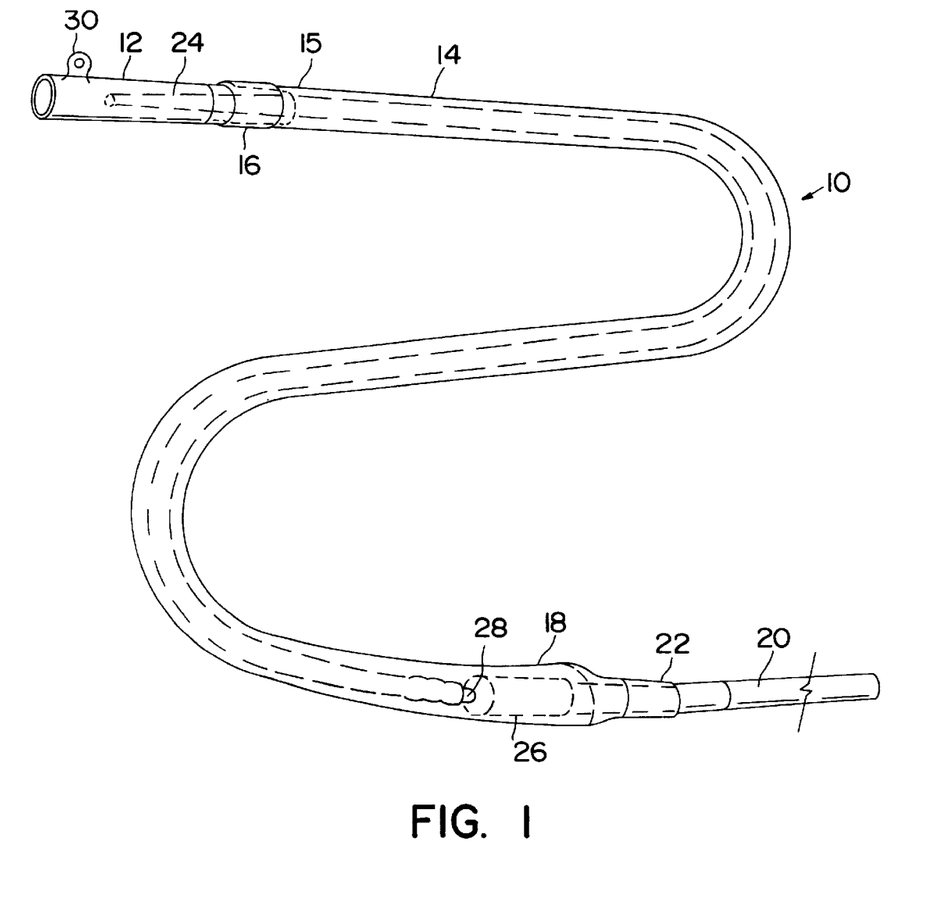
FIG. 1 illustrates a perspective view of a sleeved suction device, the present invention.

FIG. 1 illustrates a perspective view of a sleeved suction device 10, the present invention. Included in the sleeved suction device 10 is a distally located rigid end 12 of tubular plastic or other suitable material or alternative shape, as later described, a flexible plastic cover member 14, the distal end 15 of the flexible plastic cover member 14 is secured over or under one end of the rigid end 12 by tape 16 which contacts both the rigid end 12 and the flexible plastic cover member 14. In the alternative, a suitable securement method, such as heat sealing, an adhesive, rubber bands, clamps, or the like, can be used to effect a suitable fixation of the rigid end 12 to the flexible plastic cover member 14. The proximal end 18 of the flexible cover member 14 secures over one end of a suction tube 20, which leads to a suction producing device, by tape 22 which contacts the proximal end 18 of the flexible cover 14 and the suction tube 20. Any other suitable method of securement can be utilized, such as the use of glue, clamps, rubber bands, or the like. Located centrally in the sleeved suction device 10 is a flexible suction catheter tube 24. The distal end of the suction catheter 24 extends partially into and loosely aligns to the rigid end 12, through the interior of the flexible cover member 14 and secures to a connector member 26 through a ribbed connector member 28. The ribbed connector member 28 and the connector are located within the proximal end 18 of the flexible cover member 14. The distal end of the suction tube 20 suitably secures, such as by frictional engagement or gluing, to one end of the connector member 26. A hanging loop 30 or hook or other device for hanging is located on one end of the rigid member 12 so that the free end of the sleeved suction device 10 can engage a hook or other such suitable member when not in use. The components of the catheter can be made of suitable polymers which can be sterilized as necessary.

Figure 2:
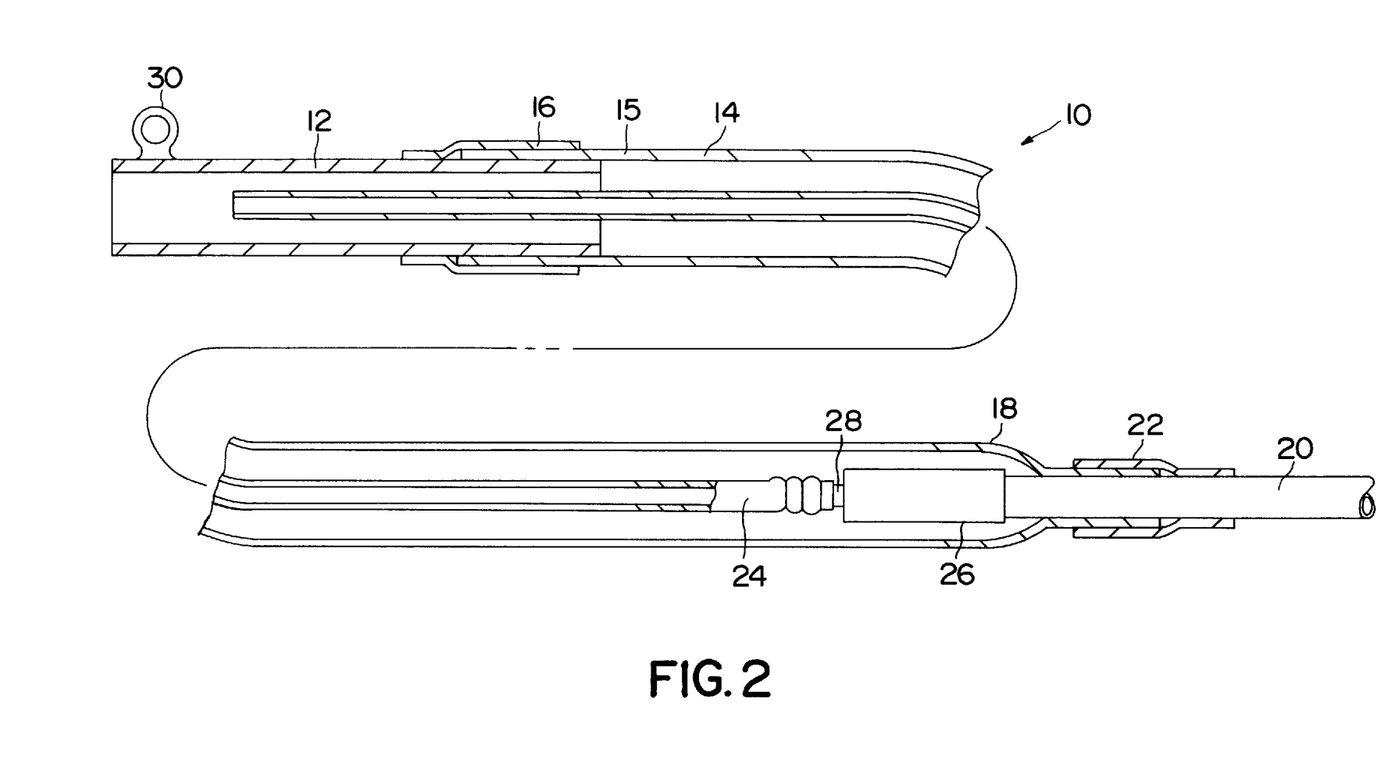
FIG. 2 illustrates a cross-sectional side view of the sleeved suction device of FIG. 1.

FIG. 2 illustrates a cross-sectional side view of the sleeved suction device 10 where all numerals correspond to those elements previously described.

MODE OF OPERATION

Figure 3:
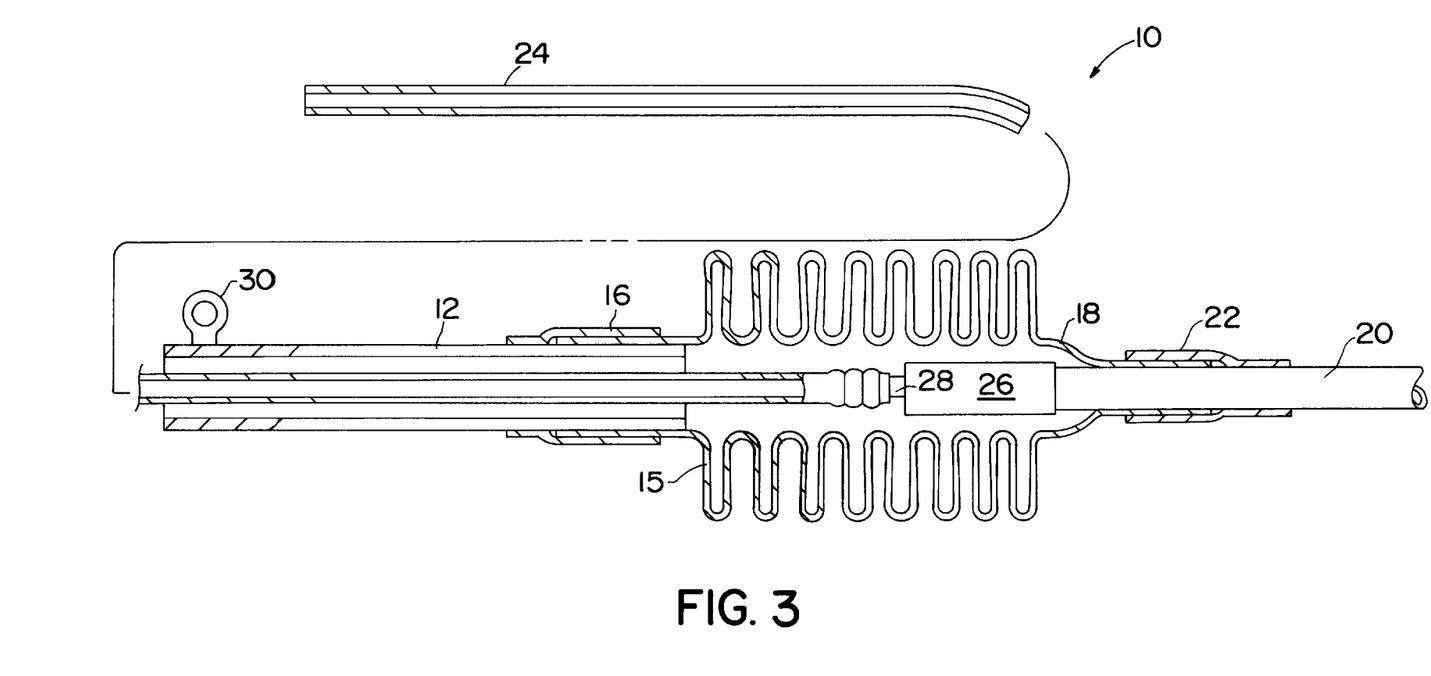
FIG. 3 illustrates the mode of operation of the sleeved suction device of FIG. 1.

FIG. 3 best illustrates the mode of operation of the sleeved suction device 10 where all numerals correspond to those elements previously described. When use of the internally located suction catheter 24 is desired, the rigid end 12 and the distal end 15 of the flexible cover member 14 are manually positioned proximally along the suction catheter 24 toward the suction tube 20 to expose the desired length of suction catheter 24. As the rigid end 12 and distal end 15 of the flexible cover member 14 are positioned proximally, the flexible cover member 14 gathers along the suction catheter 24. Full proximal positioning of the rigid end 12 over the suction catheter 24 provides a maximum gathering and generally loose compacting of the flexible cover member 14 over and about or beyond or below the area of the connector member 26. Gathering beyond the connector member 26 exposes the connector member 26 in case of the need to change or disconnect from suction. When suction is terminated, the rigid end 12 is manually positioned as far as possible in a distal direction to once again cause the rigid end 12 to position over and about the distal end of the suction catheter 24 to prevent contamination of the surrounding area by body fluids. Contamination of the distal end of the suction catheter 24 is also prevented so that it can subsequently be used again in a suction procedure with the patient.

Figure 4:
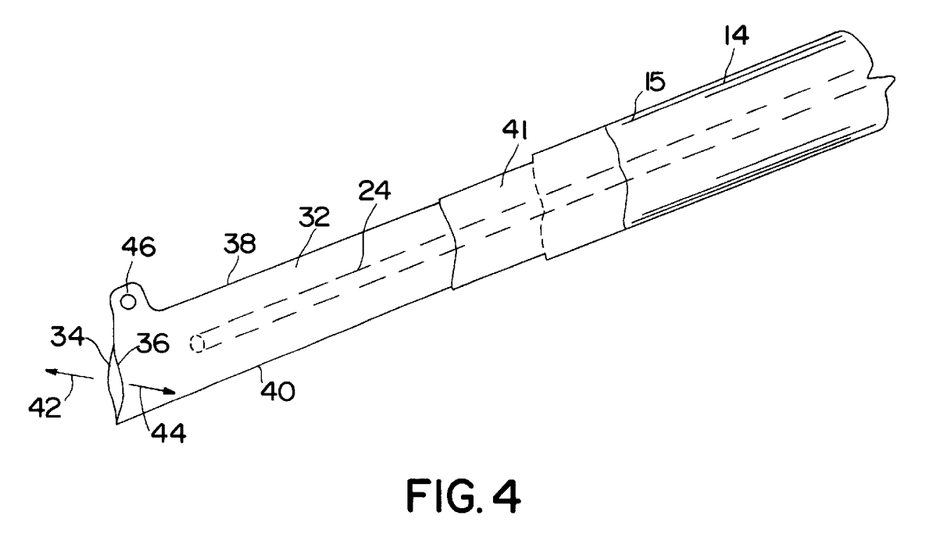
FIG. 4, an alternative embodiment, illustrates the incorporation of a flat semi-rigid end member in use with a sleeved suction device.

FIG. 4, an alternative embodiment, illustrates the incorporation of a flat semi-rigid end member 32, in lieu of the rigid end 12, for use with the sleeved suction device 10 where all numerals correspond to those elements previously described. The semi-rigid end member 32 is of one piece construction incorporating planar members 34 and 36 having common edges 38 and 40. A tape 41, or other such suitable material such as heat sealing, glue, contacts and secures the distal end of the flexible cover member 14 and the semi-rigid end member 32 to join the flexible cover member 14 and the semi-rigid end member 32. Revealing of the suction catheter 24 is initiated by manually positioning the semi-rigid end member 32 and the distal end 15 of the flexible cover member 14 proximally as previously described. This positioning action causes the planar members 34 and 36 to be forcibly and laterally displaced from their previous juxtaposition to a temporary new shape as indicated by arrows 42 and 44 to allow passage of the suction catheter 24. Subsequent to the suction procedure, the semi-rigid end member 32 is manually positioned distally until the distal end of the suction catheter 24 is fully engaged within the confines of the semi-rigid end member 32. The semi-rigid end member 32 is constructed of a plastic or other material having suitable memory thereby causing the ends of the planar members 34 and 36 to return to the memory position to mutually and fully contact each other to seal the end of the semi-rigid end member 32. In the alternative, a separable adhesive can be incorporated to effect a sealed unit which can be resealed after use for maximum sealing capabilities. Thus, a positive seal is effected to prevent contamination of the suction catheter 24 by surrounding environment and to prevent contamination of surrounding environments by body fluids resident on the suction catheter 24. Opening of the distal end of the semi-rigid end member 32 can also be effected by simultaneously exerting pressure on opposing edges 38 and 40. A hanging loop 46 or hook or other hanging member is provided.

Figure 5:
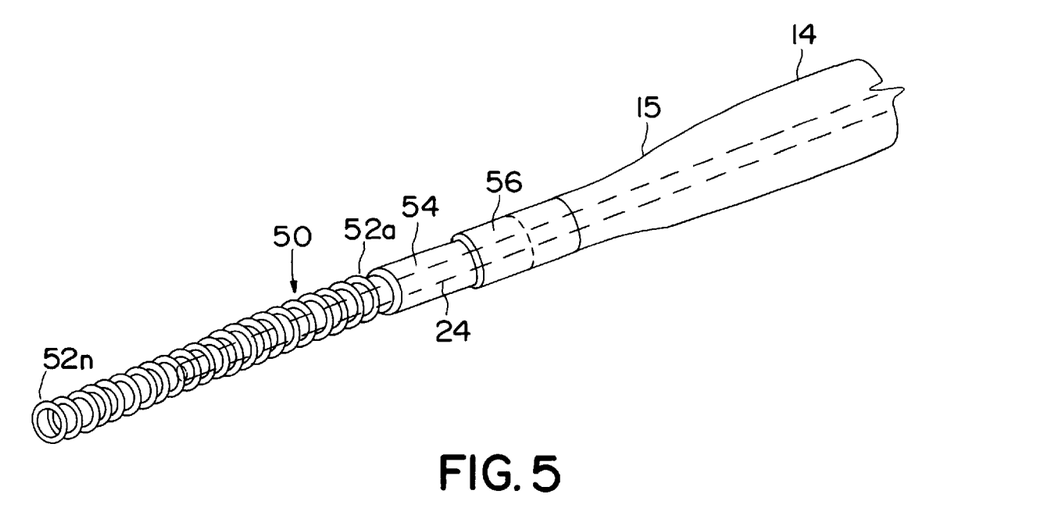
FIG. 5, an alternative embodiment, illustrates the incorporation of a bendable end member in use with a sleeved suction device.

FIG. 5, an alternative embodiment, illustrates the incorporation of a bendable or flexible end member 50 having a position memory for use in lieu of the rigid end 12 for use with the sleeved suction device 10 where all numerals correspond to those elements previously described. The bendable end member 50 is of one piece molded plastic construction incorporating a plurality of smooth ridge members 52a–52n aligned with a tubular portion 54. A tape 56, or other such suitable material such as heat sealing, glue, clamps, rubber bands, or the like, contacts and secures the proximal end of the tubular portion 54 of the bendable end member 50 to the distal end 15 of the flexible cover member 14. Revealing of the suction catheter 24 is initiated by manually positioning the bendable end member 50 and the distal end 15 of the flexible cover member 14 proximally along the suction catheter 24 as previously described. Subsequent to suction procedures, the bendable end member 50 is positioned distally to cover the suction catheter 24 and provide for prevention of contamination of the suction catheter 24 and the outer environs. The bendable end member 50, as well as having protectional qualities, can also be used as a suction catheter guide as described in FIG. 6.

Figure 6:
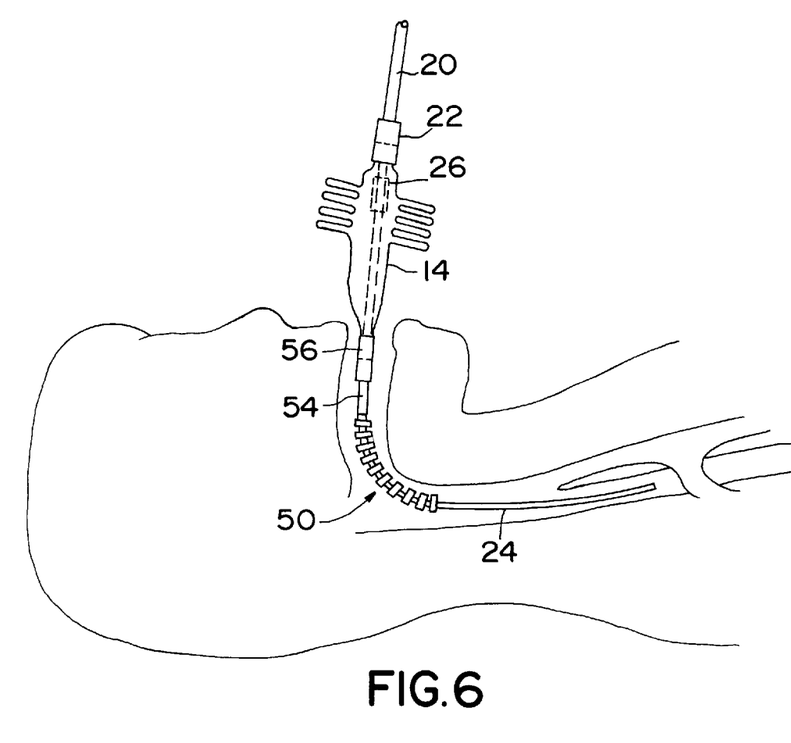
FIG. 6 illustrates the use of a bendable end member as a guide for insertion of a suction catheter into the posterior oral pharynx.

FIG. 6 illustrates the use of the bendable end member 50 as a guide for insertion of the suction catheter 24 into or through the posterior oral pharynx into the esophagus or trachea where all numerals correspond to those elements previously described. Often the problem of catheter curling is encountered when inserting a suction catheter into the posterior oral pharynx into the esophagus. This problem can be overcome by manually shaping the bendable end member 50 to conform to the general shape of the posterior oral pharynx area. The shaped bendable end member 50 is then inserted into the posterior oral pharynx and the suction catheter 24 is advanced into the esophagus while using the shaped bendable end member 50 as a guide. To advance the suction catheter 24 requires that the tubular portion 54 of the bendable end member be held static while grasping and manually advancing the suction catheter 24 through the shaped bendable end member 50. Advancement of the suction catheter 24 also advances the connector 26 and the suction tube 20, thereby causing gathering of the flexible cover member 14. Subsequent to the suction procedure, the suction catheter 24 is retracted into the bendable end member 50. The bendable end member 50 is then withdrawn and covered by an external cover if reuse is desired.

Figure 7:
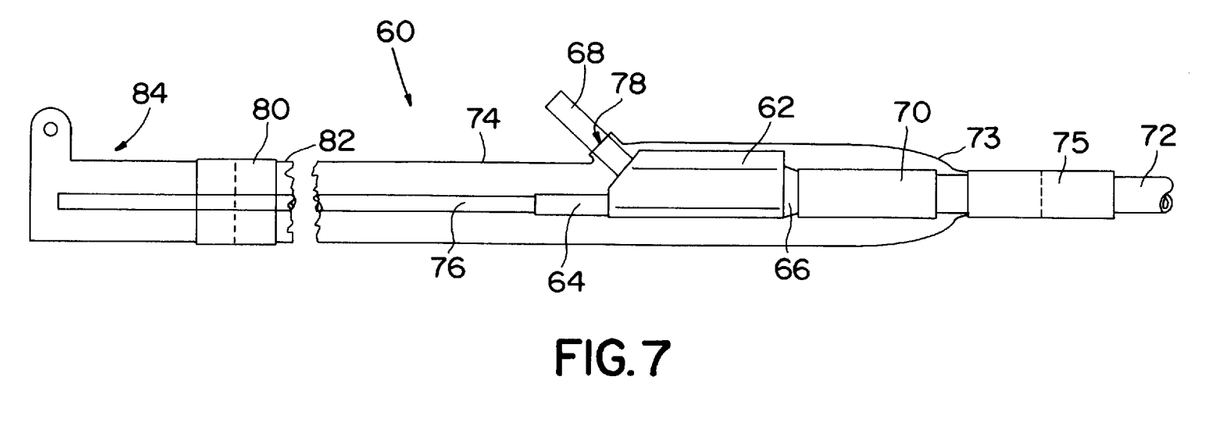
FIG. 7, an alternative embodiment, illustrates the incorporation of a suction valve with a sleeved suction device.

FIG. 7, an alternative embodiment, illustrates the use of a sleeved suction device 60 incorporated for use with a suction valve 62. The suction valve 62 includes a distal suction valve connector 64, a proximal suction valve connector 66, and a vent tube 68. A proximal connector 66 suitably attaches to a connector member 70, such as by frictional engagement or gluing. A suction tube 72 suitably attaches to the connector 70, such as by frictional engagement or gluing. The proximal end 73 of a flexible cover member 74 secures to the distal end of the suction 72 by tape 75 or other suitable method. The flexible cover member loosely aligns over the connector 70, the suction valve 62 and a suction catheter 76 extending proximally from the distal suction valve connector 64. The vent tube 68 extends through an orifice 78 in the flexible cover member 74. In the alternative, glue or adhesive can be applied to the junction of the orifice 78 and the vent tube 68 to obtain a sealed environment. An end member is secured by a tape 80 to secure the distal end 82 of the flexible cover member 74 to the end member. The incorporated end member, illustrated as member 84, can be an end member previously described, such as the rigid end 12, the semi-rigid end member 32, the bendable end member 50 or any other suitable end member. Gathering of the flexible member 74, as previously described, will occur in the area just distal to the distal suction valve connector 64 when the end member 84, or other end member, is positioned to reveal the suction catheter 76. When selective application of suction is desired, one places a finger or thumb over the vent tube 68 to control suction in the suction catheter 76.

Figure 8:
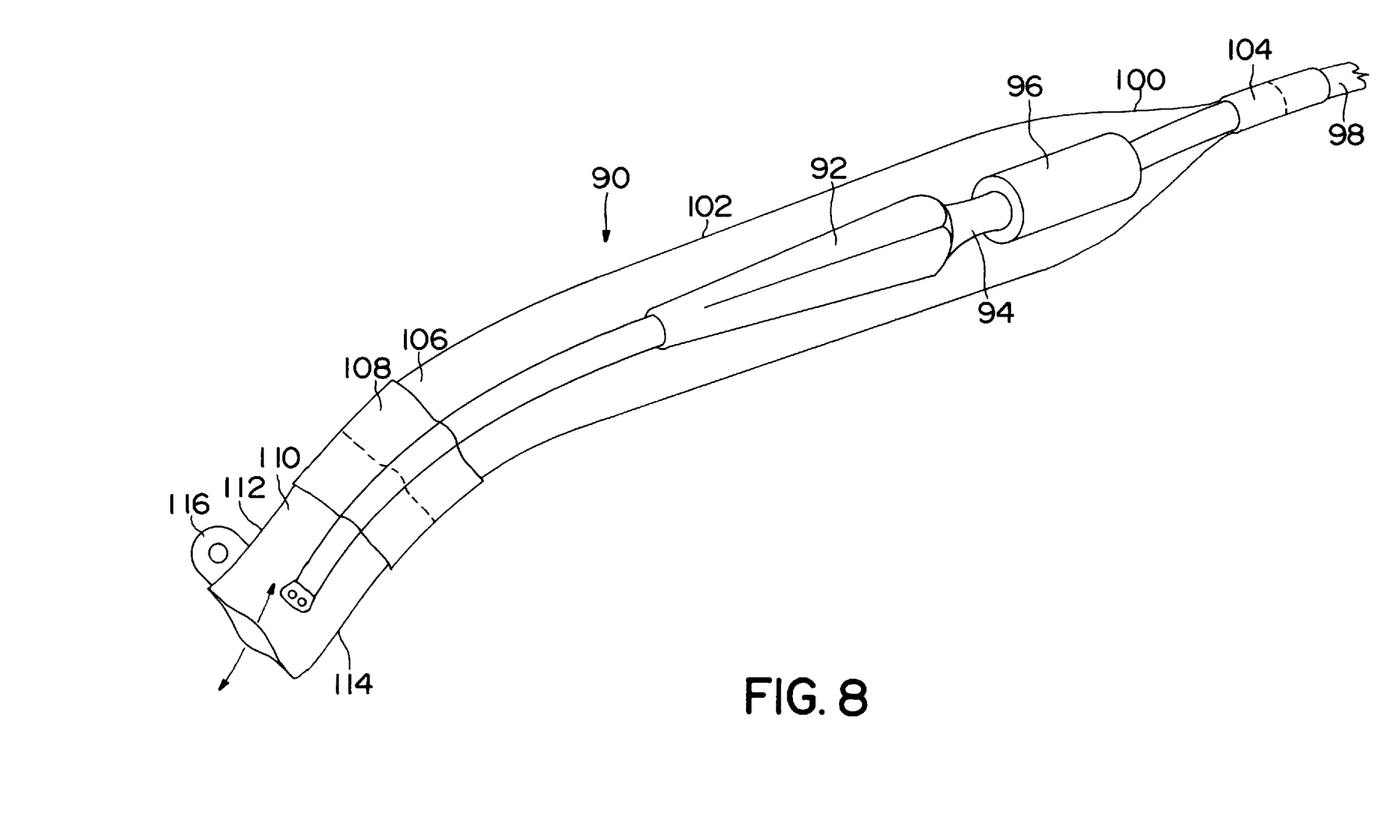
FIG. 8, an alternative embodiment, illustrates use of a sleeved suction device with a tonsil type suction device; and, FIG. 9 illustrates the operation of the sleeved suction device of FIG. 8.

FIG. 8, an alternative embodiment, illustrates the use of a sleeved suction device 90 incorporated for use with a tonsil type suction member 92. The tonsil type suction member 92 includes a proximal connector member 94 which frictionally engages or otherwise suitably attaches or connects to a connector member 96. A suction tube 98 suitably connects to the proximal end of the connector 96. The proximal end 100 of a flexible cover member 102 secures to the suction tube 98 by tape 104 or other such suitable means as previously described. The distal end 106 of the flexible cover member 102 secures by a heat seal or a tape 108 to a shortened semi-rigid end member 110 similar to the semi-rigid end member 32 illustrated and described in FIG. 4 and having edges 112 and 114 and a hanging loop or hook 116. Opening of the semi-rigid end member 110 can be effected by simultaneously exerting pressure on opposing edges 112 and 114 as previously described in FIG. 4. In the alternative, a rigid end 12, a bendable end member 50, or any other suitable end member, can be used in lieu of the semi-rigid end member 110.

Figure 9:
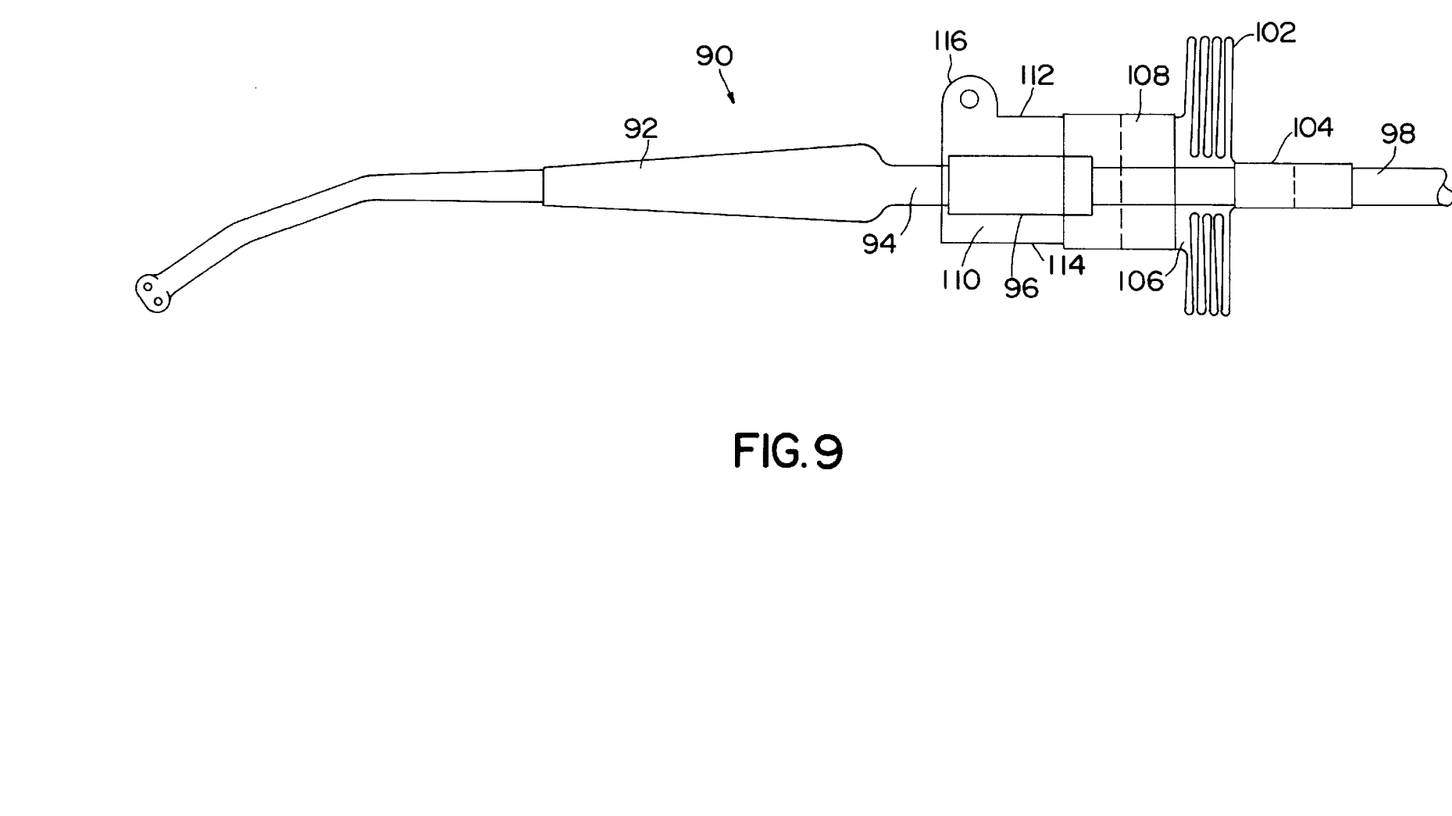

FIG. 9 illustrates operation of the sleeved suction device 90 where all numerals correspond to those elements previously described. The semi-rigid end member 110 and the distal end 106 of the flexible cover member 102 are manually positioned proximally along the tonsil type suction member 92 to reveal the tonsil type suction member 92. Gathering of the flexible cover member 102 occurs over and about or beyond and below the area proximal to the connector 96. Gathering beyond the connector member 96 exposes the connector member 96 in case of the need to change or disconnect suction without having to remove the flexible cover member 102 from the suction tube 98. Subsequent to use, the semi-rigid end member 110 is manually positioned distally to cover the tonsil type suction member 92 to protect the tonsil type suction member 92 for subsequent reuse and to protect the environment from contamination.

Various modifications can be made to the present invention without departing from the apparent scope hereof.

I claim:

1. A sleeved suction device comprising:

a. a suction tube for proximal connection to a suction producing device, the suction tube having a distal end;

b. a connector member, the connector member having a first end secured to the distal end of the suction tube and a second end having a ribbed connector member;

c. a flexible plastic cover member having a proximal end and a distal end, the proximal end of the flexible cover member secured over the suction tube, adjacent the distal end of the suction tube and adjacent the connector member by tape;

d. a rigid end member, having a first end and a second end, the first end of the rigid end member secured to the distal end of the flexible plastic cover by tape and having a hanging loop adjacent the second end; and, e. a flexible suction catheter tube, having a proximal end and a distal end, the flexible suction catheter tube located within the flexible plastic cover member and attached at the proximal end to the ribbed connector member of the connector member and having the distal end of the flexible catheter tube extending partially into and loosely aligned within rigid end member; and wherein the flexible cover member and the rigid end member can be manually, slideably, proximally, drawn back to reveal the flexible suction catheter tube and subsequently repositioned distally to cover the previously revealed flexible suction catheter tube; and wherein the flexible cover member and the rigid end member can be gathered to expose the ribbed connector member of connector member to enable uncoupling of the the flexible suction catheter tube.

2. A sleeved suction device comprising:

a. a suction tube for proximal connection to a suction source, the suction tube having a distal end;

b. a connector member, the connector member having a first end secured to the distal end of the suction tube and a second end having a ribbed connector member;

c. a flexible plastic cover member having a proximal end and a distal end, the proximal end of the flexible cover member secured over the suction tube, adjacent the distal end of the suction tube and adjacent the connector member by tape;

d. a semi-rigid bendable end member, having a first end and a second end, the first end of the semi-rigid bendable end member secured to the distal end of the flexible plastic cover by tape and having a hanging loop adjacent the second end; and, e. a flexible suction catheter tube, having a proximal end and a distal end, the flexible suction catheter tube located within the flexible plastic cover member and attached at the proximal end to the ribbed connector member of the connector member and having the distal end of the flexible catheter tube extending partially into and loosely aligned within semi-rigid bendable end member; and wherein the flexible cover member and the semi-rigid bendable end member can be manually, slideably, proximally drawn back to reveal the flexible suction catheter tube and subsequently repositioned distally to cover the previously revealed flexible suction catheter tube; and wherein the semi-rigid bendable end member retains a memory of a prior configuration and tends to return to the prior configuration.

3. A sleeved suction device comprising:

a. a suction tube for proximal connection to a suction producing device, the suction tube having a distal end;

b. a suction valve having a vent tube, a distal connector member, and a proximal connector member and wherein blocking the vent tube provide control of application of suction between the proximal connecter member and the distal connector member, the proximal connector member attached to the distal end of the suction tube, c. a flexible plastic cover member having a proximal end, an orifice located between the proximal end and a distal end, the proximal end of the flexible cover member secured over the suction tube adjacent the distal end of the suction tube and adjacent the proximal connector member by tape, the vent tube extending through the orifice;

d. an end member, having a first end and a second end, the first end of the end member secured to the distal end of the flexible plastic cover by tape and having a hanging loop adjacent the second end; and, e. a flexible suction catheter tube, having a proximal end and a distal end, the flexible suction catheter tube located within the flexible plastic cover member and attached at the proximal end to the distal suction valve connector member of the suction valve and having the distal end of the flexible catheter tube extending partially into and loosely aligned within the end member; wherein the flexible cover member and the end member can be manually, slideably, proximally, drawn back to reveal the flexible suction catheter tube and subsequently repositioned distally to cover the previously revealed flexible suction catheter tube; and wherein blocking the vent tube controls application of suction in the flexible suction catheter tube.

* * * * *